US007630473B2

(12) United States Patent
Scholz

(10) Patent No.: US 7,630,473 B2
(45) Date of Patent: Dec. 8, 2009

(54) METHOD FOR CORRECTING TRUNCATION ARTIFACTS

(75) Inventor: Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 204 days.

(21) Appl. No.: 11/729,757

(22) Filed: Mar. 29, 2007

(65) Prior Publication Data

US 2008/0123806 A1  May 29, 2008

(30) Foreign Application Priority Data

Mar. 29, 2006  (DE)  ............... 10 2006 014 629

(51) Int. Cl.
*A61B 6/00*  (2006.01)
(52) U.S. Cl. ............................. 378/18; 378/4
(58) Field of Classification Search .............. 378/4, 378/18
See application file for complete search history.

(56) References Cited

U.S. PATENT DOCUMENTS

| | | | | |
|---|---|---|---|---|
| 4,305,127 | A * | 12/1981 | Heuscher | 600/425 |
| 4,550,371 | A * | 10/1985 | Glover et al. | 378/4 |
| 6,307,909 | B1 * | 10/2001 | Flohr et al. | 378/4 |
| 6,845,141 | B2 * | 1/2005 | Flohr et al. | 378/4 |
| 7,372,935 | B2 * | 5/2008 | Bernhardt et al. | 378/4 |
| 2004/0066911 | A1 * | 4/2004 | Hsieh et al. | 378/901 |

FOREIGN PATENT DOCUMENTS

| | | |
|---|---|---|
| DE | 103 45 704 A1 | 8/2004 |
| WO | WO 2005104038 A1 * | 11/2005 |

OTHER PUBLICATIONS

Case et al., Reduction of Truncation Artifacts in Fan Beam Transmission Imaging Using a Spatially Varying Gamma Prior, IEEE Transactions on Nuclear Science, vol. 42, No. 6, Dec. 1995, pp. 2260-2265.*
Gregoriou et al., Effect of Truncated Projections on Defect Detection in Attenuation-Compensated Fanbeam Cardiac SPECT, The Journal of Nuclear Medicine, vol. 39, No. 1, Jan. 1998, pp. 166-175.*
Ohnesorge et al., Efficient correction for CT image artifacts caused by objects extending outside the scan field of view, Med Phys, 27, Jan. 1, 2000, pp. 39-46.*
Starman et al., Estimating 0th and 1st Moments in C-Arm CT Data for Extrapolating Truncated Projections, Medical Imaging, Proc. of SPIE, vol. 5747, 2005, pp. 378-387.*
Zou et al., Image Reconstruction in regions-of-interest from truncated projections in a reduced fan-beam scan, Physics in Medicine and Biology, 50, 2005, pp. 13-57.*

(Continued)

*Primary Examiner*—Edward J Glick
*Assistant Examiner*—Alexander H Taningco

(57) ABSTRACT

The invention relates to a method and an apparatus for correcting truncation artifacts in a tomographic process of an object under medical examination. To prevent truncation artifacts in a tomographic process, it is proposed to extrapolate truncated projection images by projecting an equivalent body disposed at the location of the object under examination onto an extended detector surface according to the beam geometry.

20 Claims, 4 Drawing Sheets

OTHER PUBLICATIONS

Nalcioglu et al., Limited Field of View Reconstruction in Computerized Tomography, IEEE Transactions on Nuclear Scienece, vol. NS-26, No. 1, Feb. 1979, pp. 546-551.*

Lewitt, Processing of incomplete measurement data in computed tomography, Medical Image Processing Group, Apr. 1979, pp. 412-417.*

M. Zellerhoff, B. Scholz, E.-P. Rührnschopf and T. Brunner, "Low contrast 3D-reconstruction from C-arm data", Proceedings of SPIE, Medical Imaging 2005, vol. 5745, pp. 646-655.

J. Hsieh, E. Chao, J. Thibault, B. Grekowicz, A Horst, S. McOlash and T.J. Myers, "A Novel Reconstruction Algorithm to Extend the CT Scan Field-of-View", Med. Phys. 31(9). Sep. 2004, pp. 2385-2391.

Ohnesorge et al., "Efficient correction for CT image artifacts caused by objects extending outside the scan field of view", Medical Physics 27, Jan. 1, 2000, pp. 39-46, vol. 1.

Sourbelle et al., "Reconstruction from Truncated Projections in Cone-Beam CT using Adaptive Detruncation", RSNA, 2003, pp. 1-3, Paper #1506.

Penβel et al., "Hybrid Detruncation (HDT) Algorithm for the Reconstruction of CT Data", RSNA 2004, Beitrag, 2005, pp. 1-18.

Starman et al., "Extrapolating Truncated Projections Using $0^{th}$ and $1^{st}$ Moment Constraints", RNSA 2004, Session: Physics (CT Reconstruction), Nov. 11, 2004, pp. 1-2 (abstract) and pp. 1-2, Code: SSA17-08.

* cited by examiner

US 7,630,473 B2

METHOD FOR CORRECTING TRUNCATION ARTIFACTS

CROSS REFERENCE TO RELATED APPLICATIONS

This application claims priority of German application No. 10 2006 014 629.8 filed Mar. 29, 2006, which is incorporated by reference herein in its entirety.

FIELD OF THE INVENTION

The invention relates to a method for correcting truncation artifacts in a tomographic process and an apparatus for performing the tomographic process on an object under examination.

BACKGROUND OF THE INVENTION

Such a method is known from ZELLERHOFF, M. et. al., "Low contrast 3D-reconstruction from C-Arm data", Proceedings of SPIE, Medical Imaging 2005, Vol. 5745, pages 646 to 655. The disclosed method is used to prevent truncation artifacts which occur if the object under examination extends into areas outside the so-called scan field of view. The resulting projection images are termed cut-off or truncated. Truncated projection images produce artifacts when the slices are reconstructed. In particular the image values near the edge in the slices are generally too high and too low in a central region. The slices affected by truncation artifacts are therefore of only limited diagnostic use.

In the known method, there is constructed in the edge region of a projection image, if attenuation is present there, an equivalent body which produces the same attenuation in the edge region as the object under examination. Assuming parallel beam geometry, the equivalent body is then projected on the region outside the projection image, causing the projection image to be continued in a region outside the projection image.

The equivalent body is projected onto regions outside the projection image using parallel beam geometry, even though a divergent beam geometry, e.g. a fan beam, is actually present. The equivalent body is also adapted to the image values in the edge region of the projection image on the basis of a parallel beam geometry. In this respect, errors in correcting the truncation artifacts may be induced.

The known method has the advantage, however, that no resorting of the fan beam data into parallel beam data is necessary. Resorting of the fan beam data into parallel beam data is also termed rebinning. So-called rebinning is very compute intensive and cannot be used in every case. Particularly in the case of C-arm computed tomography recordings, the wait and compute times required for this purpose are not available because of the already very long image reconstruction times.

A method in which resorting of the fan beam data into parallel beam data is performed is known from HSIEH, J. et al., "A novel reconstruction algorithm to extend the CT scan field-of-view", MED. PHYS. 31 (9), September 2004, pages 2385 to 2391. After resorting, an equivalent body is reconstructed and the equivalent body is projected with parallel beam geometry onto regions outside the projection image. In this respect this is a correct method from a theoretical standpoint.

SUMMARY OF THE INVENTION

Proceeding from this prior art, the object of the invention is therefore to specify a method for correcting truncation artifacts which is improved in respect of reducing truncation artifacts and can be carried out with comparatively low computational cost/complexity.

This object is achieved by a method having the features set forth in the independent claims. Advantageous embodiments and further developments are detailed in claims dependent thereon.

For the method, wherein:
divergent radiation is emitted by a radiation source,
an object under examination is transilluminated by the divergent radiation in different projection directions,
the radiation penetrating the object under examination is measured by a detector, and
projection images recorded by the detector are extended by extrapolation by determining an equivalent body which attenuates the radiation issuing from the radiation source according to the object under examination in the edge region of the projection image, and also by determining for extrapolated pixels the radiation attenuation caused by the equivalent body outside the projection image.

For the method, the equivalent body is disposed in the region of the object under examination. To determine the image values of extrapolated pixels outside the projection image, the attenuation of the beams passing from the radiation source to the pixels is observed. The method therefore requires no resorting of the fan beam data into parallel beam data. As the equivalent body is projected onto the surface of the detector corresponding to the actual beam geometry, the truncation artifacts are in practice effectively reduced, the computational complexity being lower than for converting data assigned to a divergent beam into parallel beam data.

In a preferred embodiment, the radiation incident on a row of detector elements forms a fan of beams. In this case extrapolation is then performed in one direction along the row of detector elements if the image values at the end of the row of detector elements show attenuation. In this case extrapolation is only performed if required. In addition, the extrapolation for each row can be individually adapted to the image values of the particular row.

In a further preferred embodiment, the equivalent body has a circular cross-section in the plane of the fan of beams. The position of the equivalent body and its radius can then be determined on the basis of the value and gradient of the image values at the edge of the projection image. This assumes, however, that the center of the circular cross-section of the equivalent body can only be shifted with one degree of freedom in the plane of the fan.

In addition, it is also possible to use an equivalent body having an elliptical cross-section and to adapt the cross-section of the equivalent body on the basis of the value, gradient and curvature of the image values at the edge of the projection image. This case also assumes that the elliptical cross-section of the equivalent body can only be shifted with one degree of freedom in the plane of the fan.

The method is preferably a method for correcting truncation artifacts of projection images recorded during x-ray computed tomography with the aid of x-rays. If human or animal bodies are examined using the method, water is preferably selected as the material for the equivalent body.

With the method, a projection image can be extrapolated in the plane of the fan in the direction of the row of detector elements. However, the method can also be used for adjacent tows of detector elements, for example, if the beam is a cone beam.

BRIEF DESCRIPTION OF THE DRAWINGS

Further features and advantages of the invention will emerge from the following description in which exemplary embodiments of the invention are individually explained with reference to the accompanying drawings in which.

DETAILED DESCRIPTION OF THE INVENTION

Figure 1:
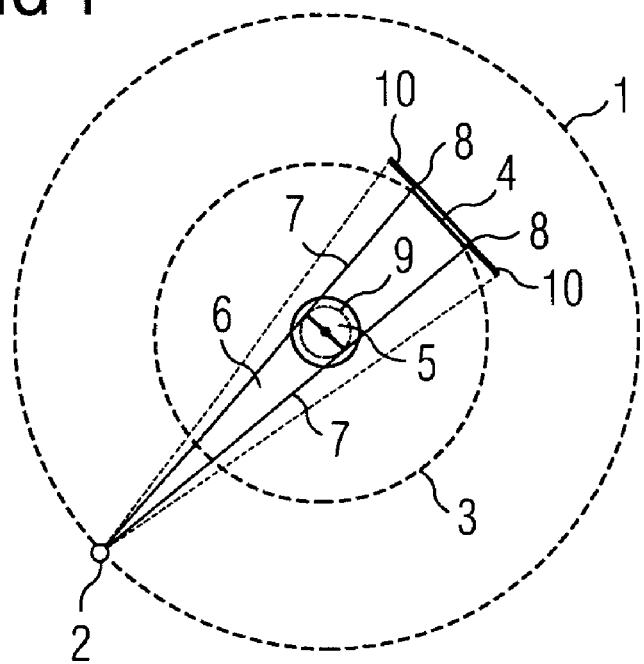
FIG. 1 shows the path of a detector and a radiation source around an object under examination viewed in the axial direction.

FIG. 1 shows an axial view of a circular path 1 of an x-ray radiation source 2 and a circular path 3 of an x-ray detector 4 around an object under examination 5. The x-ray detector 4 is preferably a digital flat-panel detector or large-area detector. The object under examination 5 can be, for example, an animal or human body.

From a beam focus, the x-ray radiation source 2 emits a fan of beams 6, the edge beams 7 of which are incident on edges 8 of the x-ray detector 4.

The x-ray radiation source 2 and the x-ray detector 4 orbit the object 5 in such a way that the x-ray radiation source 2 and the x-ray detector 4 are on opposite sides of the object 5. With the concerted movement of x-ray detector 4 and x-ray radiation source 2, the edge beams 7 of the fan of beams 6 define a field of view 9 which, if the object 5 is excessively large, lies partially or even completely inside the object under examination 5. The regions of the object 5 outside the field of view 9 are therefore not imaged onto the x-ray detector 4. Consequently, truncated projection images of the object 5 are recorded by the x-ray detector 4 in some cases. From the truncated projection images, slices of the object under examination 5 are reconstructed by a processing unit (not shown in the drawing) connected downstream of the x-ray detector 4. The truncated projection images produce truncation artifacts when slices of the transilluminated object 5 in the plane of the fan 6 are reconstructed. In particular, image values of the reconstructed slice are too high in edge regions, while the image values inside the slice are too low. Even if the object under examination 5 uniformly attenuates the beams of the fan of beams 6 emitted by the x-ray radiation source, an image value profile running across the slice therefore exhibits a somewhat dished characteristic.

Excessively high image values mean that an excessively large attenuation by the object 5 of the x-ray radiation emitted by the x-ray radiation source 2 is shown in the reconstructed slice, whereas excessively low image values indicate an excessively low attenuation by the object 5.

In order to reduce the occurrence of truncation artifacts in the reconstructed slice, the recorded projection image is extrapolated at the edges 8 of the x-ray detector 4 onto an extended detector surface 10. Reconstruction is then performed on the basis of the augmented projection images, thereby enabling truncation artifacts in the reconstructed slice to be effectively reduced.

This will now be explained in greater detail with reference to the object 5 shown in FIG. 2.

Figure 2:
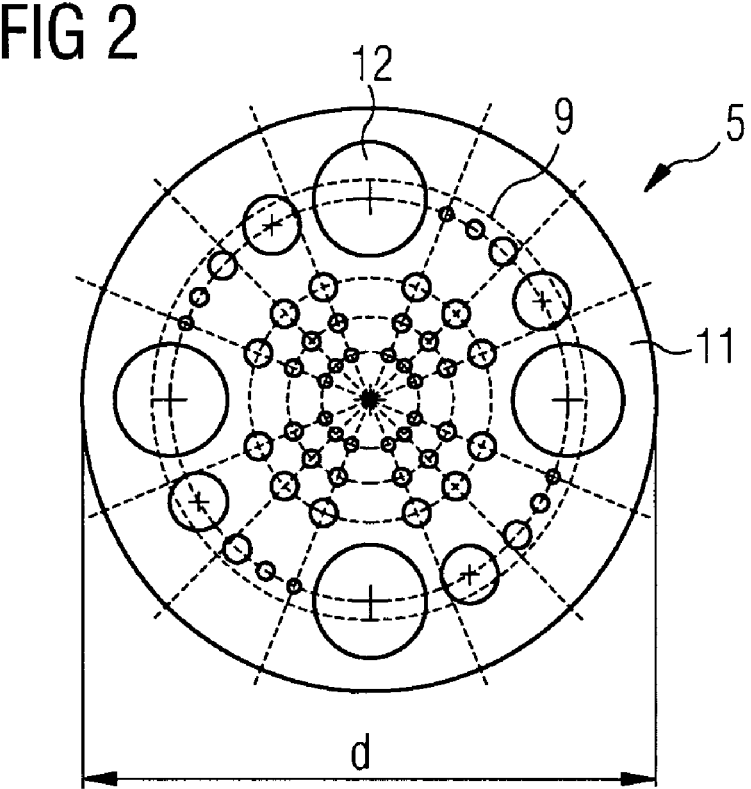
FIG. 2 shows a cross-section through a body phantom used for checking the imaging quality, viewed in the axial direction.

The representation of the object 5 shown in FIG. 2 is a cross-section through a body phantom 11 which can be used for testing computed tomography devices. The body phantom 11 has three different contrast layers each having inserts 12 of different density. A low-contrast layer has inserts 12 with the values 3 HU, 5 HU, 10 HU and 15 HU. An average contrast layer has inserts 12 with densities of 20 HU, 25 HU, 30 HU and 40 HU. The outer diameter d of the body phantom 11 is dimensioned such that some of the outer inserts 12 lie outside the field of view 9.

Figure 3:
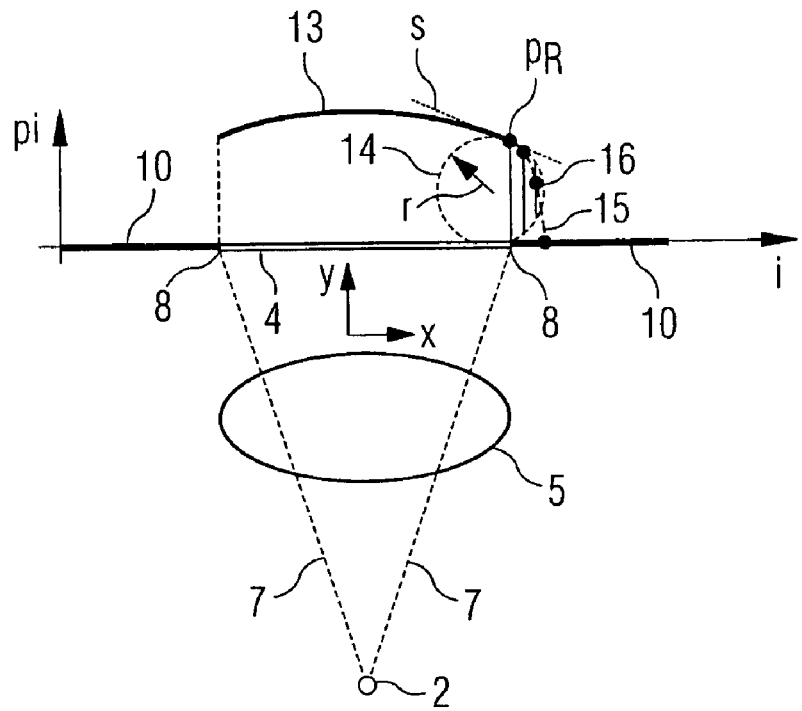
FIG. 3 shows a prior art correction method for suppressing artifacts.

FIG. 3 shows a prior art extrapolation method.

The radiation emerging from the focus of the x-ray radiation source 2 penetrates the object under examination 5 and is incident on the x-ray detector 4. Using detector elements of a row which are indexed with column index i, the x-ray detector 4 records projection values $p_i$ which form a projection value profile 13 between the edges 8 of the x-ray detector 4 in row direction.

In order to extrapolate the projection value profile 13 in row direction to the extended detector surface 10, on the edge 8 of the x-ray detector 4 a water cylinder 14 is determined which under parallel beam geometry causes the same attenuation at the edges 8 as the object 5 in the region of the edge beam 7. As parallel beam geometry is assumed, the location of the water cylinder 14 in beam direction y is irrelevant.

The center position x of the water cylinder 14 at right angles to the beam direction y and the radius r of the water cylinder 14 are selected such that the projection value $p_R$ and the gradient s of the projection value profile 13 at the edge 8 coincide with the projection value and gradient of an extrapolated projection value profile 15 resulting from the parallel projection of the water cylinder 14 onto the extended detector surface 10.

Extrapolation values 16 can then be determined on the basis of the water cylinder 14.

The height of the water cylinder 14 is equal to the spacing of the detector rows in column direction, which means that the object 5 is continued slice by slice.

As will be explained in detail below, the prior art extrapolation method is not suitable for sufficiently reducing truncation artifacts in every case.

Figure 4:
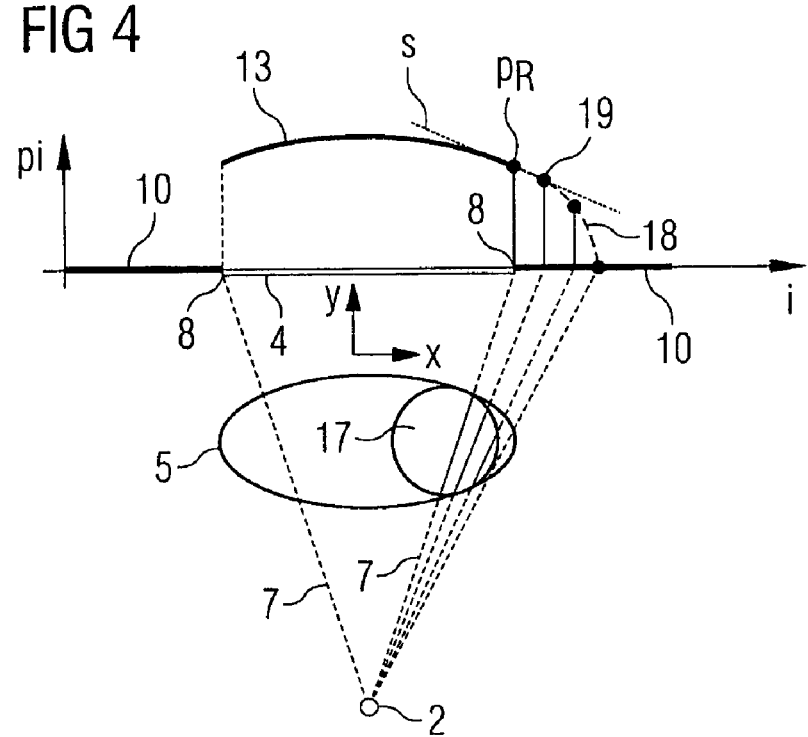
FIG. 4 shows a correction method according to the invention.

FIG. 4 shows a extrapolation method for reducing truncation artifacts that is an improvement on the prior art. In the method illustrated in FIG. 4, a water cylinder 17 disposed in the region of the object 5 is determined and projected onto the extended detector surface 10 according to the geometry of the fan of beams 6. The position of the water cylinder 17 in beam direction y is preferably close to a center line of the object 5. The center position x at right angles to the beam direction y and the radius of the water cylinder 17 are determined such that a projection value $p_R$ and the gradient of the projection value profile 13 at the edge 18 of the x-ray detector 4 coincide with the projection value and gradient of the extrapolated projection value profile 18.

By projecting the water cylinder 17 onto the extended detector surface 10, extrapolation values 19 can then be determined.

The fact that the extrapolation method described with reference to FIG. 4 results in much better truncation artifact reduction compared to the prior art emerges particularly clearly from FIGS. 5 to 10.

Figure 5:
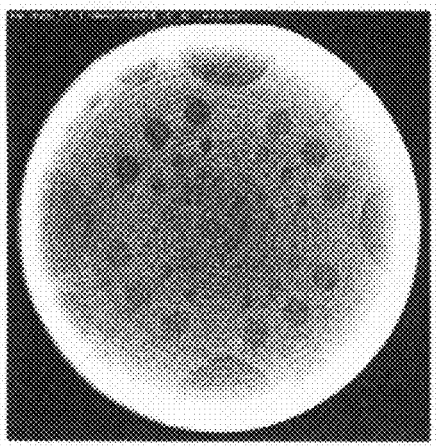
FIGS. 5 and 6 show reconstructions of an average contrast layer of the body phantom from FIG. 2 using the prior art method and the method according to the invention.
Figure 6:
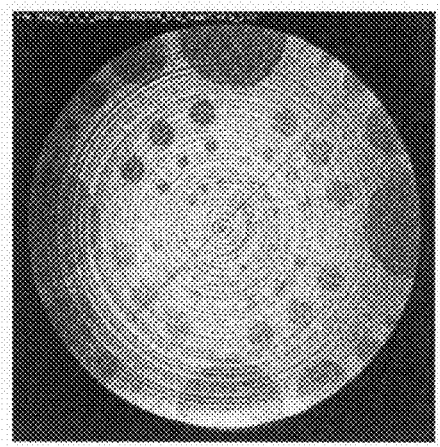

FIG. 5 shows the reconstructed truncated average contrast layer of the body phantom 11 from FIG. 2 when the extrapolation method according to FIG. 3 is used. The excessive increase in the projection values in the edge regions of the slice are clearly visible. With the slice in FIG. 6, on the other hand, the body phantom 11 was reconstructed using the extrapolation method shown in FIG. 4. In FIG. 6 the outlines of the inserts 12 are also clearly visible in edge regions of the projection image.

Figure 7:
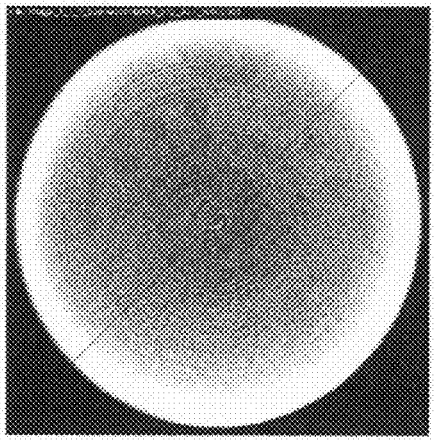
FIGS. 7 and 8 show reconstructions of a low-contrast layer of the body phantom from FIG. 2 using the prior art method and the method according to the invention.
Figure 8:
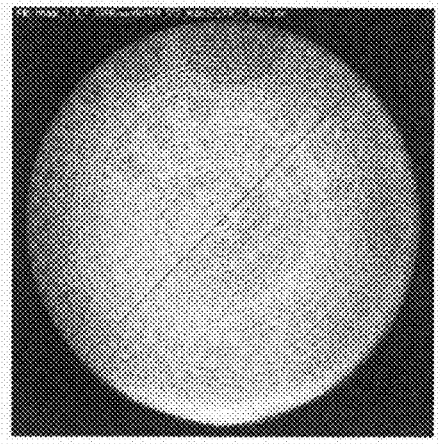

Clear differences also emerge in the low-contrast region. FIG. 7 shows the reconstruction of the truncated low-contrast layer of the body phantom 11 using the extrapolation method from FIG. 3. Once again the edge regions of the reconstructed slice are clearly overheightened. On the other hand, for the slice shown in FIG. 8 which was created using the extrapolation method described in FIG. 4, no overheightening is visible in the edge regions.

Looking at FIGS. 5 to 8 together also shows that, when using the conventional method shown in FIG. 3, the image values of the slice are reduced in the isocenter.

Figure 9:
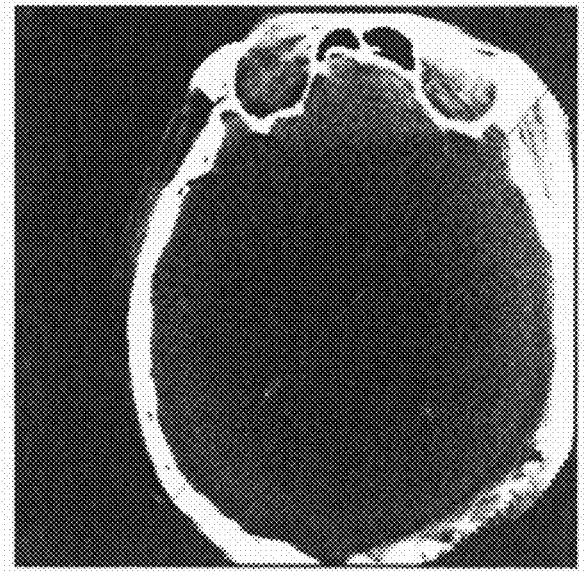
FIGS. 9 and 10 show reconstructions of a truncated recording of a patient's skull according to the prior art and the method according to the invention.
Figure 10:
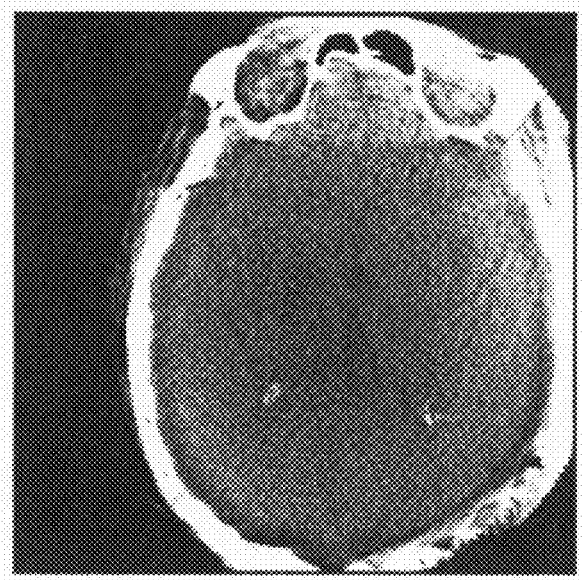

This is also clear from FIGS. 9 and 10 which contain slices with identical windowing.

FIG. 9 shows a truncated slice through a patient's skull which was created using the conventional extrapolation method shown in FIG. 3. In FIG. 9 no further details are visible in the region of the brain substance.

In the slice shown in FIG. 10, on the other hand, which was created using the method shown in FIG. 4, details indicating cerebral bleeding are also visible in the region of the brain substance.

These details are only visible in FIG. 9 when the window center is lowered. This shows that, because of the truncation artifacts, excessively low image values have been reconstructed in the center of the image.

Note that for the method illustrated in FIG. 4 water cylinders with elliptical cross-section can be used instead of the water cylinder 17 with circular cross section. In this case adaptation to the curvature of the projection value profile 13 is also possible.

It should also be noted that the projection value profile 13 used for adapting the water cylinders 17 is preferably produced using an averaging method in order to eliminate noise-induced excursions.

As in the case of the method shown in FIG. 4 no resorting from fan beam to parallel beam data is necessary, the computational complexity is kept within bounds. The method shown in FIG. 4 can therefore also be employed in computed tomography using C-arm systems.

The invention claimed is:

1. A method for correcting a truncation artifact in a tomographic process of an object under a medical examination, comprising:
    emitting a divergent radiation to the object by a radiation source, wherein the divergent radiation is a fan of radiation beams coming from a focus of the radiation source;
    transilluminating the object by the divergent radiation in a projection direction;
    measuring the radiation penetrating the object by a detector;
    recording a projection image of the object by the detector detecting the radiation at the projection direction;
    disposing an equivalent body in a region of the object;
    projecting the equivalent body onto an extended surface of the detector according to a geometry of the fan of the radiation beams without resorting the fan of the radiation beams to a parallel of the radiation beams;
    determining the equivalent body that attenuates the radiation based on the object in an edge region of the projection image;
    determining a radiation attenuation caused by the equivalent body for an extrapolated pixel outside the projection image;
    determining the extrapolated pixel outside the projection image based on the radiation attenuation;
    extending the projection image by an extrapolation based on the extrapolated pixel; and
    using the projection image in the medical examination.

2. The method as claimed in claim 1, wherein the detector comprises a row of detector elements that detect the divergent radiation.

3. The method as claimed in claim 2, wherein the projection image at an edge of the row of detector elements is extrapolated in a row direction.

4. The method as claimed in claim 1, wherein the extrapolation is performed if at least one image value of the project image at an edge of the detector shows an attenuation.

5. The method as claimed in claim 1, wherein the equivalent body is a cylindrical equivalent body.

6. The method as claimed in claim 5,
    wherein the cylindrical equivalent body comprises a circular cross-section, and
    wherein a center position and a radius of the cylindrical equivalent body are determined as a function of a value and a gradient of a projection value profile at an edge of the detector.

7. The method as claimed in claim 5,
    wherein the cylindrical equivalent body comprises an elliptical cross-section, and
    wherein a center position and semiaxes of the cylindrical equivalent body are determined as a function of a value, a gradient and a curvature of a projection value profile at an edge of the detector.

8. The method as claimed in claim 1,
    wherein the extrapolation is performed for adjacent rows of detector elements of the detector, and
    wherein a height of the equivalent body equals to a spacing of the adjacent rows of detector elements.

9. The method as claimed in claim 1, wherein the radiation source is an x-ray radiation source and the detector is an x-ray detector.

10. The method as claimed in claim 1, wherein the object is a human or animal body and the equivalent body comprises water.

11. An apparatus for performing a tomographic process on an object under a medical examination, comprising:
    a radiation source that emits a divergent radiation to the object, wherein the divergent radiation is a fan of radiation beams coming from a focus of the radiation source;
    a detector that records a projection image of the object by detecting the divergent radiation;
    an equivalent body disposed in a region of the object that attenuates the radiation and is projected onto an extended surface of the detector according to a geometry of the fan of the radiation beams without resorting the fan of the radiation beams to a parallel of the radiation beams; and a calculation device that:
  determines a shape of the equivalent body based on the object in an edge region of the projection image,
  determines a radiation attenuation caused by the equivalent body for an extrapolated pixel outside the projection image,
  determines the extrapolated pixel outside the projection image based on the radiation attenuation, and
  extends the projection image by an extrapolation based on the extrapolated pixel.

12. The apparatus as claimed in claim 11,
wherein the detector comprises a row of detector elements that detect the divergent radiation.

13. The apparatus as claimed in claim 11, wherein the projection image at an edge of the row of detector elements is extrapolated in a row direction.

14. The apparatus as claimed in claim 11, wherein the extrapolation is performed if at least one image value of the project image at an edge of the detector shows an affenuation.

15. The apparatus as claimed in claim 11, wherein the equivalent body is a cylindrical equivalent body.

16. The apparatus as claimed in claim 15,
wherein the cylindrical equivalent body comprises a circular cross-section, and
wherein a center position and a radius of the cylindrical equivalent body are determined as a function of a value and a gradient of a projection value profile at an edge of the detector.

17. The apparatus as claimed in claim 15,
wherein the cylindrical equivalent body comprises an elliptical cross-section, and
wherein a center position and semiaxes of the cylindrical equivalent body are determined as a function of a value, a gradient and a curvature of a projection value profile at an edge of the detector.

18. The apparatus as claimed in claim 11,
wherein the extrapolation is performed for adjacent rows of detector elements of the detector, and
wherein a height of the equivalent body equals to a spacing of the adjacent rows of detector elements.

19. The apparatus as claimed in claim 11, wherein the radiation source is an x-ray radiation source and the detector is an x-ray detector.

20. The apparatus as claimed in claim 11, wherein the object is a human or animal body and the equivalent body comprises water.

* * * * *